United States Patent
Chinn et al.

(10) Patent No.: US 6,416,548 B2
(45) Date of Patent: *Jul. 9, 2002

(54) ANTIMICROBIAL ANNULOPLASTY RING HAVING A BIODEGRADABLE INSERT

(75) Inventors: Joseph A. Chinn; R. Michael Casanova, both of Austin, TX (US)

(73) Assignee: Sulzer Carbomedics Inc., Austin, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/357,584

(22) Filed: Jul. 20, 1999

(51) Int. Cl.⁷ .................................................. A61F 2/24

(52) U.S. Cl. .................... 623/2.36; 623/2.38; 623/2.41; 623/1.42; 623/901

(58) Field of Search ................................ 623/2.36, 1.42, 623/2.38, 2.41, 901

(56) References Cited

U.S. PATENT DOCUMENTS

| | | | |
|---|---|---|---|
| 3,511,684 A | 5/1970 | Huffaker | 117/47 |
| 3,585,647 A | 6/1971 | Gajewski et al. | 3/1 |
| 4,055,861 A | * 11/1977 | Carpentier et al. | 623/2.36 |
| 4,107,121 A | 8/1978 | Stoy | 260/29.6 |
| 4,254,180 A | 3/1981 | Kline | 428/323 |
| 4,326,532 A | 4/1982 | Hammar | 128/349 |
| 4,331,697 A | 5/1982 | Kude et al. | 427/2 |
| 4,442,133 A | 4/1984 | Greco et al. | 427/2 |
| 4,521,564 A | 6/1985 | Solomon et al. | 525/54.1 |
| 4,526,714 A | 7/1985 | Feijen et al. | 260/112 |
| 4,600,652 A | 7/1986 | Solomon et al. | 428/423.3 |
| 4,634,762 A | 1/1987 | Feijen et al. | 530/350 |
| 4,642,242 A | 2/1987 | Solomon et al. | 427/2 |
| 4,676,974 A | 6/1987 | Hofmann et al. | 424/9 |
| 4,678,660 A | 7/1987 | McGary et al. | 424/25 |
| 4,678,671 A | 7/1987 | Feijen et al. | 424/443 |
| 4,749,585 A | 6/1988 | Greco et al. | 427/2 |
| 4,895,566 A | 1/1990 | Lee | 604/266 |
| 4,917,686 A | 4/1990 | Bayston et al. | 604/265 |
| 4,952,419 A | 8/1990 | De Leon et al. | 427/2 |
| 4,973,493 A | 11/1990 | Guire | 427/2 |
| 4,979,959 A | 12/1990 | Guire | 623/66 |
| 5,053,453 A | 10/1991 | Ku | 525/54.1 |
| 5,103,306 A | 4/1992 | Weiman et al. | 358/133 |

(List continued on next page.)

OTHER PUBLICATIONS

US 5,556,632, 09/1996, Kohler et al. (withdrawn)
Chacques, J. C., et al., Absorbable Rings for Pediatric Valvuloplasty, SupplementIV Circulation vol. 82, No. 5, Nov. 1990, pp. 82–88.

(List continued on next page.)

*Primary Examiner*—Corrine McDermott
*Assistant Examiner*—Choon P. Koh
(74) *Attorney, Agent, or Firm*—Blossom E. Loo; Timothy L. Scott

(57) ABSTRACT

This invention provides an antimicrobial annuloplasty rings, and methods for making the same, wherein the annuloplasty rings have a desired degree of initial rigidity to facilitate ease of handling during implantation but which becomes flexible some time after implantation. The annuloplasty ring contains a relatively rigid insert enclosed by a fabric sheath, the insert being at least partly comprised of a biodegradable material. Following surgical implantation of the annuloplasty ring, the rigid insert component of the ring, upon exposure to blood and/or other physiological fluids, undergoes a controlled biodegradation which decreases its rigidity, thereby increasing the flexibility of the implanted annuloplasty ring. Furthermore, at least some portion of the annuloplasty ring of the invention has incorporated therein one or more antimicrobial agents in a manner which reduces the likelihood of device infection following implantation.

28 Claims, 2 Drawing Sheets

U.S. PATENT DOCUMENTS

| | | | |
|---|---|---|---|
| 5,104,407 A | 4/1992 | Lam et al. | 623/2 |
| 5,263,992 A | 11/1993 | Guire | 623/66 |
| 5,286,763 A * | 2/1994 | Gerhart et al. | 514/772.4 |
| 5,308,641 A | 5/1994 | Cahalan et al. | 427/2 |
| 5,414,075 A | 5/1995 | Swan et al. | 568/333 |
| 5,512,329 A | 4/1996 | Guire et al. | 427/508 |
| 5,624,704 A | 4/1997 | Darouiche et al. | 427/2.24 |
| 5,679,659 A | 10/1997 | Verhoeven et al. | 514/56 |
| 5,716,397 A | 2/1998 | Myers | 623/2 |
| 5,741,551 A | 4/1998 | Guire et al. | 427/407.1 |
| 5,865,814 A | 2/1999 | Tuch | 604/265 |
| 5,877,263 A | 3/1999 | Patnaik et al. | 525/453 |

OTHER PUBLICATIONS

Olanoff, L. S., et al., Sustained Release of Gentamicin from Prosthetic Heart Valves,American Society for Artificial Internal Organs vol. XXV, 1979, pp. 334–338.

Burkoth,A., et al., A New Class of Hotopolymerizable Surface Eroding Polymers for Medical Applications,Surfaces in Biomaterials Foundation, 1997, pp. 58–63.

Solomon,D. D., et al., Antibiotic Releasing Polymers,Journal of Controlled Release, 6(1987), pp. 343–352.

Mee, R. B. B., et al., Congenital Heart Surgery,Current Science, 1992, pp. 249–258.

Chachques,J. C., et al., Current Status of Valvularsurgery, Current Opinion in Cardiology, 1994, 9:186–190.

Raad, I., et al., Effect of Anti–Infective Coatings on Biofilms,Surfaces in Biomaterials Foundation 1996, pp. 5–8.

Sherertz, R. J., et al., Efficacy of Dicloxacillin–Coated Polyurethane Catheters in Preventing Subcutaneous Staphylococcus Aureus Infection in Mice, Antimicrobial Agents and Chemotherapy, Aug. 1989, pp. 1174–1178.

Hirudin Immobilization to Produce Antithrombic Surfaces, Cardiovascular Science and Technology: Basic and Applied Dec. 1–3, 1990.

Anderson, A. B., et al., Photochemical Immobilization of Heparin to Reduce Thrombogenesis, 20th Annual Meeting of the Society for Biomaterials, Apr. 5–9, 1994, p. 75.

Chachques, J. C., et al., Study of Muscular and Ventricular Function in Dynamic Cardiomyoplasty: A Ten–Year Follow–Up, The Journal of Heart and Lung Transplantation, vol. 16, No. 8, pp. 854–868.

* cited by examiner

ANTIMICROBIAL ANNULOPLASTY RING HAVING A BIODEGRADABLE INSERT

FIELD OF THE INVENTION

This invention relates generally to devices for use in the surgical repair of heart pathologies, and, more particularly, to antimicrobial annuloplasty rings which contain relatively rigid biodegradable inserts.

DESCRIPTION OF THE RELATED ART

Human heart valves can become deformed or otherwise damaged by any of a number of processes brought on by normal aging and/or disease pathologies. For example, degenerative diseases can cause the valve annulus to become enlarged to the point where the leaflets attached to it cannot fully close. This situation, known as valve incompetence, eventually requires surgical correction by valve repair or replacement procedures. Of the surgical options available for valve reconstruction, valvular annuloplasty represents the procedure most frequently performed, particularly for the tricuspid and mitral valves. Valvular annuloplasty is an operation whereby ring-shaped devices or bands, known as annuloplasty rings, are sewn to the distended valve annulus in order to restore it to its normal, undilated circumference.

Annuloplasty rings are most typically either highly flexible or are stiff and comparatively rigid. Rigid rings typically consists of an open wire element completely covered with cloth. The wire is somewhat stiff yet resiliently deformable and is not intended to be removable from the cloth covering. These annuloplasty rings, because of their rigidity, lie flat and maintain their somewhat oval shape during implantation. Although a rigid ring's oval shape has been claimed to enhance the competence of the repaired valve, its rigidity can also impede the beneficial flexing movements of the native annulus during the cardiac cycle. Flexible annuloplasty rings generally consist of a soft core of elastomeric material, e.g., silicone rubber, completely enclosed by a sheath of biocompatible cloth. Because of their flexibility, these rings can be difficult to handle during surgical manipulations and generally must be supported during implantation by a holder which is subsequently removed before tying off the implanting sutures.

To overcome some of the deficiencies of flexible and rigid ring structures, an annuloplasty ring would desirably be stiff during handling and implantation, but then become flexible after implantation. As disclosed in U.S. Pat. No. 5,716,397, an annuloplasty ring may consist of a flexible ring into which a rigid structure is inserted to provide temporary rigidity during implantation. Once the ring is implanted and tested, the rigid structure may be removed. However, this approach requires undesirable additional handling after the ring is implanted. Another annuloplasty ring, as disclosed in U.S. Pat. No. 5,104,407, consists of a ring constructed partially of a flexible material and partially of a rigid material. Unfortunately, this ring will be difficult and costly to manufacture and will suffer from the drawbacks afflicting both flexible and rigid rings. In an alternative approach, Chachques et al. (Circulation 82(5), Supplement IV, 82–88, 1990) describes absorbable prosthetic rings for use in pediactric valvular annuloplasty. The rings are reported to address concerns over secondary valvular stenosis in children that can result from implantation of known annuloplasty rings. The rings described by Chachques et al. are synthesized from biodegradable polydioxanone and covered with a porous extensible sewing sheath to allow contact between the polydioxanone, the blood and the endocardium. As a result of this contact, the polydioxanone ring is reported to undergo degradation following implantation.

Colonization of microorganisms on the surfaces of annuloplasty rings and other implantable medical devices can produce serious and costly complications, including the need to remove and/or replace the implanted device and/or vigorous treatment of secondary infections. Although infection of implanted medical devices is a relatively infrequent complication associated with their clinical use, the threat to infected patients, and the cost to the medical care system, are significant.

Numerous approaches for providing antimicrobial surfaces and/or devices have been described in the art. Unfortunately, such approaches have had only limited success. For example, although coating a material with immobilized antimicrobial compounds has been reported to effectively reduce bacterial colonization of devices in a laboratory setting, similar results have been difficult to replicate in the clinical setting. To be effective in vivo, antimicrobial agents immobilized on the surface of a medical device preferably should intimately contact the colonizing bacteria that has infected the device. Unfortunately, many clinically relevant bacteria produce a slimy protective substance called biofilm within which they grow. This biofilm, among other things, prevents direct contact of the bacterial cells with a substrate surface to which they adhere, making the bacteria resistant to otherwise toxic materials that may be present on the substrate surface.

In the laboratory, the antimicrobial efficacy of medical devices that have been treated in one way or another in attempt to confer some degree of antimicrobial activity to the device, has often been evaluated by exposing the devices to bacterial cultures. The selection and source of bacteria for such testing is critical to obtaining meaningful results, since it is now known that microorganisms floating free in a cell culture (called planktonic bacteria) behave differently than those adherent to a substrate, such as a bacterial culture vessel or an implanted medical device. Planktonic bacteria are more susceptible to antimicrobial agents immobilized on a surface than are biofilm-producing bacteria. Thus, devices coated with immobilized antimicrobial agents may effectively prevent colonization of planktonic bacteria in the laboratory, but may be completely ineffective in preventing infection of devices by clinically relevant biofilm-enclosed bacteria. As a result, the experimental use of planktonic bacteria cultured in the laboratory, rather than biofilm bacteria derived from clinical infections, has led to the commercialization of numerous antimicrobial medical devices lacking clinical efficacy.

To effectively inhibit biofilm bacterial growth, an antimicrobial agent should preferably penetrate the biofilm. To achieve this, the antimicrobial agent should be able to diffuse from the surface of the medical device following implantation. Therefore, antimicrobial agents immobilized on the surface of a medical device, and therefore not subject to diffusion, have less than optimal activity against many clinically relevant microorganisms. A more effective medical device will have the ability to deliver diffusable antimicrobial agent to the local environment following implantation.

Various methods have been described for coating or otherwise incorporating antimicrobial agents into or onto medical devices in a manner which allows for their release into the local environment of an implanted medical device. For example, U.S. Pat. No. 5,624,704 reports a method for impregnating a non-metallic medical implant with an antimicrobial agent by first dissolving the antimicrobial agent in an organic solvent to form an antimicrobial composition. Thereafter, a separate penetrating agent and alkalinizing agent must be added to the antimicrobial composition. The antimicrobial composition is then applied to a medical device of interest in order to cause the incorporation of the composition into the material of the medical device. Thus, the method of U.S. Pat. No. 5,624,704 teaches the necessity of using additional components, i.e., penetrating and alkalinizing agents, in a dissolved antimicrobial composition, in order to achieve effective incorporation into the medical device. Unfortunately, the use of these additional components can substantially increase the materials and processing costs associated with such a method, and can also lead to degradation of the antimicrobial agents.

The present invention is directed to providing alternatives to the currently available annuloplasty rings which overcome, or at least reduce the effects of, one or more of the problems set forth above.

SUMMARY OF THE INVENTION

This invention provides an antimicrobial annuloplasty ring having sufficient initial rigidity, i.e., prior to implantation, to facilitate ease of handling during surgical manipulations, but which becomes flexible to a desired extent following implantation. The foregoing is accomplished by use of a relatively rigid biodegradable annuloplasty ring insert as a component of an annuloplasty ring. Upon implantation of an annuloplasty ring containing a biodegradable ring insert of this invention, the insert undergoes degradation in the patient's body as a result of its contact with blood and/or other physiological fluids. The degradation of the biodegradable insert causes a decreasing degree of rigidity of the annuloplasty ring as the insert material is degraded and/or resorbed by the patient's body.

Therefore, in one aspect of the present invention, there is provided an annuloplasty ring which comprises a biodegradable ring insert and a fabric sheath enclosing the ring insert, wherein the fabric sheath and/or the biodegradable insert have undergone one or more antimicrobial treatment processes. The ring insert portion of the annuloplasty ring is at least partly comprised of a biodegradable material selected from any of a variety of biodegradable polymers, including polyanhydrides, polyglycolides, polylactides, polyorthoesters, and other like materials. In one illustrative embodiment, the biodegradable insert is comprised of a highly cross-linked polyanhydride material, particularly one that is photopolymerizable, such as that produced by the photopolymerization of methacrylate anhydride monomers. The fabric sheath which encloses the biodegradable insert, or the biodegradable insert itself, is preferably treated either before, after, or simultaneous with the fabrication of the annuloplasty ring in a manner which causes the incorporation of one or more antimicrobial agents into or onto the fabric sheath.

In a further aspect of the invention, there is provided a method for making an antimicrobial annuloplasty ring by forming a biodegradable ring insert at least partly comprised of a material selected, for example, from polyanhydrides, polyglycolides, polylactides and polyorthoesters, and enclosing the ring insert within a fabric sheath. The ring insert may be formed as a solid part, may be comprised of fibrous materials, or some combination thereof, and is fabricated by any of a variety conventional techniques available for forming shaped articles from polymeric materials, including, without limitation, extrusion, molding, machining, casting, spinning, and other like processes. At some point during fabrication and/or assembly of the annuloplasty ring, or after assembly but prior to implantation, at least some portion of the ring insert and/or the fabric sheath, or some other component of the annuloplasty ring, is treated by an antimicrobial treatment process in order to cause the incorporation of at least some antimicrobial agent into or onto a desired portion or portions of the annuloplasty ring.

BRIEF DESCRIPTION OF THE DRAWINGS

The invention may be understood by reference to the following description taken in conjunction with the accompanying drawings, in which like reference numerals identify like elements, and in which.

Figure 1A:
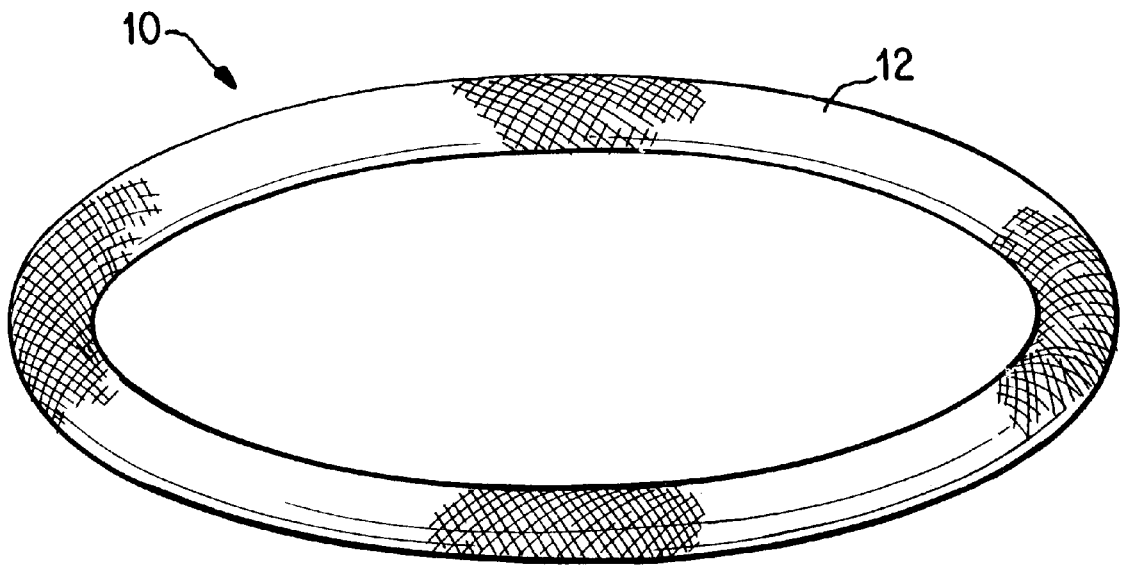
FIG. 1A illustrates one embodiment of the present invention in which the annuloplasty ring is a complete ring.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claim.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 1B:
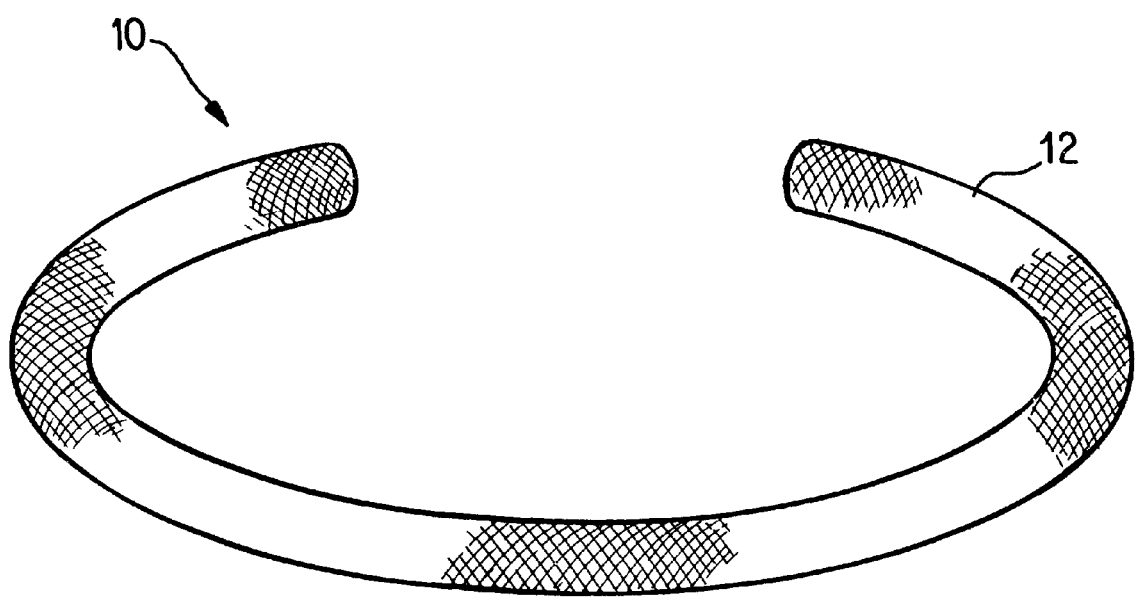
FIG. 1B illustrates one embodiment of the present invention in which the annuloplasty ring is an incomplete ring.
Figure 2:
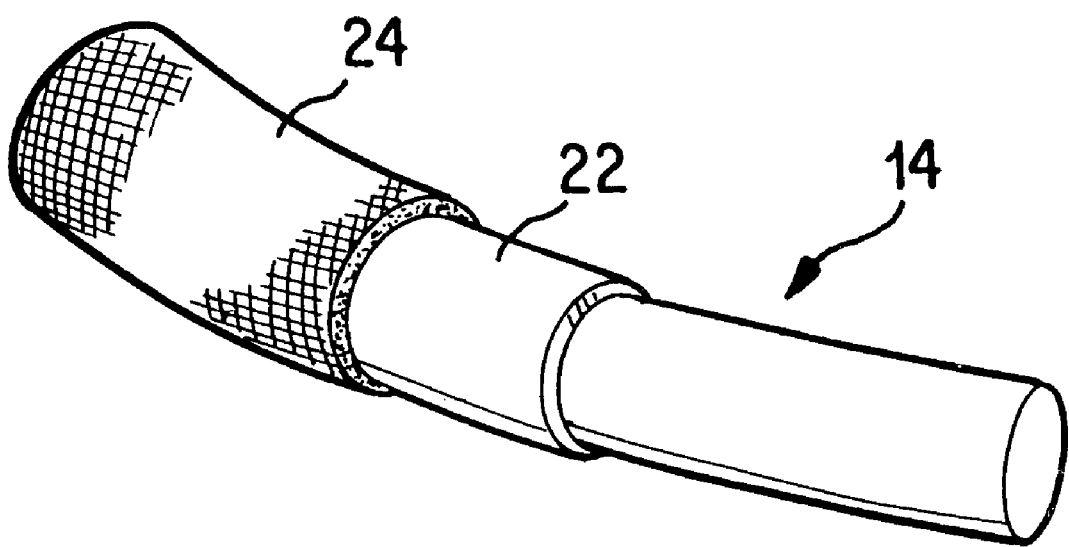
FIG. 2 illustrates a partial section of an annuloplasty ring according to one embodiment of the present invention, showing the positional relationship between the biodegradable ring insert, the covering material, and the outer fabric sheath.

FIGS. 1A and 1B depict two illustrative annoloplasty rings, 10 and 10a, respectively, according to the present invention. The annuloplasty rings each comprise a biodegradable ring insert (not shown) and a sheath 12 enclosing the biodegradable insert, the sheath 12 being constructed of a biocompatible material. The annuloplasty ring 10 of FIG. 1A represents a complete, i.e., closed, annuloplasty ring, whereas the annuloplasty ring 10 of FIG. 1B represents an incompete ring. In FIG. 2, a partial section of an annuloplasty ring is shown in order to illustrate the biodegradable ring insert 14 enclosed within the fabric sheath 24. FIG. 2 further depicts an elastomeric-like covering material 22 positioned between the ring insert 14 and the fabric sheath 24, which may be desired for certain embodiments. As described herein, the fabric sheath 24, the elastometric-like covering material 22 andlor the ring insert 14 will have incorporated therein or thereon one or more antimicrobial agents to provide protection from infection following implantation of the device.

The biodegradable annuloplasty ring insert of the present invention is generally comprised of one or more materials capable of being formed into a desired ring shaped article which has a sufficent degree of rigidity and which degrades with acceptable kinetics upon exposure to the physiological environment into which an annuloplasty ring is implanted. Examples of materials suitable for use in forming a biodegradable insert according to this invention may include, without limitation, polyanhydrides, polylactides, polyglycolides, dextran, hydroxyethyl starch, gelatin, derivatives of gelatin, polyvinylpyrolidone, polyvinyl alcohol, poly-N-(2-hydroxypropyl)methacrylamide, polyglycols, polyesters, poly(orthoesters), poly(ester-amides) and other like materials.

In one preferred aspect of the present invention, the material used to form the biodegradable insert is selected from "surface eroding" polymers, e.g., those which undergo a controlled degradation primarily along the surface of the insert, rather than a material which undergoes bulk degradation and is more subject to fragmentation. Such materials are generally characterized by a substantially microscopic degradation, rather than one which results in the generation of macroscopic particulate matter. By employing surface eroding polymers in the fabrication of the ring insert, there is a reduced possibility of embolic complications associated with the release of fragments of the insert material during degradation. Such fragments may become lodged in the fabric sheath which surrounds the insert, possibly leading to an undesirable inflammatory response, or may make their way into the blood stream of the patient, possibly leading to a stroke. Surface eroding polymers suitable for use in forming a biodegradable ring insert according to this invention may include, for example, polyanhydrides and poly-orthoesters.

One particularly illustrative surface eroding polymer that may be used for forming a biodegradable ring insert is a polyanhydride. A cross-linked polyanhydride material may be produced using essentially any synthetic approach available to the skilled individual. In one example, a polyanhydride material may be produced from photopolymerizable methacrylate anhydride monomers. Dimethacrylated anhydride monomers may be synthesized, for example, from precursor diacid molecules of sebacid acid or 1,6-bis(p-carboxyphenoxy)-hexane, as described in Anseth et al. (Surfaces in Biomaterials, 1997 Symposium Notebook, pgs. 58–62). The resulting monomers may be polymerized into homopolymers or copolymers by dissolving a suitable photoinitiator, such as 2,2-dimethoxy-2-phenylacetophenone (DMPA, Ciba Geigy) or camphorquinone (CQ, Aldrich) and ethyld-4-N,N-dimethylaminobenzoate (4EDMAB, Aldrich), in the monomer at a concentration typically ranging from about 0.01 wt. % to about 10 wt. %. Polymerization may be initiated with ultraviolet light, visible light, or with another suitable energy source, at an intensity and for a duration effective to produce the desired polymeric material. Other photopolymerizable anhydride monomers, and their methods of synthesis and polymerization into cross-linked polyanhydride networks are known and will also be apparent to the skilled individual in view of this disclosure.

The biodegradable materials used for fabricating an annuloplasty ring insert according to this invention will advantageously exhibit controllable biodegradability, bioresorbability, and/or overall biocompatibility within living tissue. Of course, it is preferred that the biodegradable insert material is substantially biocompatible, such that both the insert material and the products resulting from its degradation are physiologically benign, e.g., are not overly toxic to the point of compromising the outcome of the annuloplasty procedure or the health of the patient. The biodegradation of these materials will preferably result in degradation products having a physiologically neutral pH, or having a pH sufficiently near to physiological neutrality that the products do not induce any pH-related disturbances in or around the tissue into which the annuloplasty ring is implanted. It should be recognized that variations in the degradation rate of the ring insert may depend not only on the characteristics of the insert composition, but also on the overall health of the patient, variations in anticipated immune reactions of the patient to the implant, the site of implantation, and other clinical indicia.

The degradation kinetics and mechanical properties of the biodegradable insert may be independently controlled. For example, the skilled individual will recognize that the initial rigidity of the biodegradable insert may vary somewhat depending on the composition of the insert, but that this parameter is quite controllable through the manipulation of synthesis, cross-linking, and/or other processing conditions, to provide the insert with a desired rigidity. By controlling the cross-linking density of a polyanhydride material, e.g., by varying the molecular weight between the double bonds, the mechanical properties of the resulting cross-linked polyanhydride material can be altered from being quite flexible to highly rigid. Moreover, by changing the hydrophobicity of the monomer molecules or comonomer mixture that is reacted, the degradation time scale of the final polymer network may be controlled. For example, a significant increase in the degradation rate occurs as the amount sebacic acid is increased in copolymers produced from sebacid acid and 1,6-bis(p-carboxyphenoxy)-hexane. Polyanhydride homopolymers comprised of cross-linked sebacid acid degrade within a matter of days, while homopolymers of 1,6-bis(p-carboxyphenoxy)-hexane degrade in approximately one year (Anseth, 1997). Thus, by copolymerizing sebacic acid and 1,6-bis(p-carboxyphenoxy)-hexane at various ratios, copolymers can be provided with desired degradation kinetics.

The method of making the biodegradable insert is not specifically restricted, and is limited only by the techniques available in the art for forming shaped articles from polymeric materials. The ring insert may be comprised of a solid article, may be a fibrous article constructed, for example, of cabled fibers, woven or non-woven fabric, or may be a combination of solid and fibrous materials. Typically, the devices are composed of substantially solid articles which are fabricated from the biodegradable materials described herein using conventional polymer processing techniques such as injection molding, gel or melt extrusion, machining, and the like. A ring insert containing some fibrous component may be fabricated using conventional fiber-forming techniques such as melt spinning, gel spinning, solution spinning, dry spinning, etc. Such processing techniques and procedures are well known in the art and will not be described herein in further detail.

Preferably, the biodegradable insert will be fabricated using conventional molding techniques, wherein polymerization and/or cross-linking occur either in the mold or just prior to filling the mold, depending on the properties and characteristics of the material being used. In one illustrative process, monomer molecules are provided in an appropriate medium within a mold having the desired ring or partial ring geometry and a suitable stimulus is applied to effect polymerization and/or cross-linking within the mold. For example, when using the methacrylated anhydride monomers described above, polymerization may be effected in the presence of a photoinitiator by exposure of the mold to an appropriate light source, generally in the ultraviolet or visible spectrum, at an intensity and for a duration effective to result in the desired degree of polymerization and/or cross-linking of the material within the mold. Of course, in this situation, the mold will be one that is comprised of a material that is sufficiently transparent to the light energy necessary to effect polymerization.

As is known in the art, the shape of the biodegradable insert will generally be that of an oval or annular shaped partial or complete ring, although other shapes could be tailored, as desired, for the unique requirements of a given implementation. A partial, incomplete ring, i.e., one having a shape similar to the letter "C", may be preferred over a completely closed ring in that it allows for a somewhat improved degree of manipulation during surgical implantation.

In addition to the biodegradable insert described above, the annuloplasty ring of this invention will generally further comprise an extensible fabric sheath surrounding the biodegradable insert. The use of a cloth or fabric mesh to enclose various plastic and/or metal members which are subsequently surgically implanted in the human body is known. Such polymeric sheaths are typically comprised of a fabric or fabric-like polymeric material having a relatively high porosity, and are made by conventional techniques. For example, the sheath may be a fabric material made from polyethyleneterephthalate, polytetrafluoroethylene, polyester (polyacetate), polyethylene, or other such materials known in the art. During implantation, the sheath serves to facilitate surgical fixation of the annuloplasty ring by the surgeon. In addition, during biodegradation of the insert in the patient, the fabric sheath may advantageously participate in the fibroblastic reaction occurring at the site of implantation involving interstitial fibroblast proliferation as well as production of elastin and collagen fibers.

It is generally preferred that the porosity of the fabric sheath is sufficiently high to allow an adequate flow of physiological fluids and other materials necessary to stimulate degradation of the biodegradable insert. However, the porosity of the sheath should not be so high that unacceptably large fragments of biological insert may reach the bloodstream if such fragments are released during degradation of the insert. In this regard, one important advantage of using a surface eroding biodegradable polymer described herein for the production of a ring insert is that these materials do not release undesirably large particulate fragments during degradation. Consequently, there is a reduced risk of embolic complications when surface eroding polymers are employed, even when used in conjunction with fabric sheaths of very high porosity.

In one preferred embodiment of the invention, as depicted in FIG. 2, the annuloplasty ring may further comprise a flexible, elastomeric-like covering material 22 surrounding the biodegradable ring insert 14, positioned between the ring insert 14 and the fabric sheath 24. For example, the ring insert may be inserted into or otherwise enclosed within a material such as silicone rubber, poly(ether urethane), polytetraflouorethylene, or other like materials. This may be most readily achieved by inserting the biodegradable insert into a length of elastomeric tubing having an appropriate internal diameter similar to or slightly smaller than the diameter of the biodegradable insert. The use of these elastomeric tubing materials in modem annuloplasty rings is well known and therefore not described in further detail herein. Once the biodegradable ring insert is enclosed within this elastomeric covering, the insert and covering are then inserted and sealed within the described fabric sheath prior to use.

As would be apparent to the skilled individual in this art, other materials and/or compounds may be combined before, during, or subseqent to formation of one or more of the compenents of the present annuloplasty ring, or added to, coated onto, etc, during or after its fabrication. These compounds may include essentially anything which will not unacceptably interfere with the desired properties of the biodegradable insert, e.g., its desired initial rigidity, its biodegradability, and/or its ability to degrade into components that are substantially innocuous to living systems. Examples of such substances may include, without limitation, plasticizers, stabilizers, pigments, dyes, radio-opaque materials, lubricants, antioxidants, bioactive agents, antithrombogenic agents, and the like.

According to the present invention, at least some portion of the annuloplasty ring described above has incorporated therein one or more antimicrobial agents, preferably in a manner which allows for some degree of diffusion of the antimicrobial agents following implantation. For example, one or more antimicrobial agents may be incorporated into or onto the biodegradeable ring insert 14, the elastometric-like covering 22, or, more preferably, the fabric sheath 24 (See FIG. 2). Numerous antimicrobial treatment processes have been described for causing the incorporation of anti-microbial and other bioactive agents into or onto a medical device, and the skilled individual would recognize the applicability of such approaches to the present invention.

"Antimicrobial agent", as used herein, refers to essentially any antibiotic, antiseptic, disinfectant, etc., or combination thereof, effective for inhibiting the viability and/or proliferation of one or more microorganisms. Numerous classes of antibiotics are known and may be suitable for use in accordance with this invention. Such antibiotics may include, but are not necessarily limited to, tetracyclines (e.g., minocycline), rifamycins (e.g., rifampin), macrolides (e.g., erythromycin), penicilins (e.g., nafcillin), cephalosporins (e.g., cefazolin), other beta-lactam antibiotics (e.g., imipenem and aztreonam), aminoglycosides (e.g., gentamicin), chloramphenicol, sufonamides (e.g., sulfamethoxyazole), glycopeptides (e.g., vancomycin), quinolones (e.g., ciprofloxacin), fusidic acid, trimethoprim, metronidazole, clindamycin, mupirocin, polyenes (e.g., amphotericin B), azotes (e.g., fluconazole), beta-lactam inhibitors, etc.

Examples of illustrative antibiotic agents that may be used in accordance with the present invention include minocycline, rifampin, erythromycin, nafcillin, cefazolin, imipenem, aztreonam, gentamycin, sulfamethoxazole, vanomycin, ciprofloxacin, trimethoprim, metronidazole, clindamycin, telcoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, nystatin, and other like compounds. The antibiotics used in accordance with this invention will generally be selected so as to have relatively low water solubility such that their period of dissolution into the body is prolonged. Moreover, it may be desired for many applications that one or more antimicrobial agents having distinct modes of action are incorporated into the annuloplasty ring in order to broaden its range of antimicrobial activity.

Suitable antiseptics and disinfectants for use in this invention may include, for example, hexachlorophene, cationic bisiguanides (e.g., chlorohexidine, chclohexidiene, etc.), iodine and iodophores (e.g., povidone-iodine), parachlorometa-xylenol, furan medical preparations (e.g., nitrofurantoin, nitrofurazone), methenamine, aldehydes (glutaraldehyde, formaldehyde, etc.), alcohols, and the like.

In one illustrative embodiment of the present invention, the antimicrobial agent used to treat an annuloplasty ring according to this invention is comprised of minocycline, rifampin, or a mixture thereof. Minocycline is a semisynthetic antibiotic derived from tetracycline that functions by inhibiting protein synthesis. Rifampin is a semisynthetic derivative of rifamycin B, a macrocyclic antibiotic compound produced by the mold, *Streptomyces mediterranic*. Rifampin inhibits bacterial DNA-dependent RNA polymerase activity and is bactericical in nature. Both minocycline and rifampin are commercially available, are soluble in numerous organic solvents, and are active against a wide range of gram-positive and gram-negative organisms.

Various methods can be employed to incorporate the desired antimicrobial agents into or onto some portion of the annuloplasty ring. One such method of coating the devices involves applying or absorbing to the surface of the medical device a layer of tridodecylmethyl ammonium chloride (TDMAC) surfactant followed by a coating layer of antibiotic combination. For example, a medical device having a polymeric surface, such as polyethylene, silastic elastomers, polytetrafluoroethylene or Dacron, can be soaked in a 5% by weight solution of TDMAC for 30 minutes at room temperature, air dried, and rinsed in water to remove excess TDMAC. The device carrying the absorbed TDMAC surfactant coated can then incubated in a solution of the desired antibiotic combination, washed in sterile water to remove unbound antibiotic and stored in a sterile package until ready for implantation. In general, the solution of antibiotic combination in this method is composed of a concentration of about 0.01 mg/ml to 50 mg/ml of each antibiotic in an aqueous pH 7.4–7.6 buffered solution or sterile water. Alternative processes and reagents for bonding antibiotics to surfactant coated implantable medical devices are provided, for example, in U.S. Pat. Nos. 4,442,133, 4,678,660 and 4,749,585, the entire contents of which are incorporated herein by reference.

A further method useful to coat the surface of medical devices with the desired antibiotics can involve first coating the selected surfaces with benzalkonium chloride followed by ionic bonding of the antibiotic composition. See, e.g., Solomon, D. D. and Sherertz, R. J., J. Controlled Release 6:343–352 (1987) and U.S. Pat. No. 4,442,133. In another method, antibiotics can be dispersed within uncured silicone rubber prior to molding and curing of the material in its device configuration (Olanoff, et al., *Trans. Am. Soc. Artif Intern. Organs*, XXV, 334–338 (1979). Additional illustrative methods of coating surfaces of medical devices with antibiotics can be found in U.S. Pat. No. 4,895,566 (a medical device substrate carrying a negatively charged group having a pKa of less than 6 and a cationic antibiotic bound to the negatively charged group); U.S. Pat. No. 4,917,686 (antibiotics are dissolved in a swelling agent which is adsorbed into the matrix of the surface material of the medical device); U.S. Pat. No. 4,107,121 (constructing the medical device with ionogenic hydrogels, which thereafter absorb or ionically bind antibiotics); U.S. Pat. No. 5,013,306 (laminating an antibiotic to a polymeric surface layer of a medical device); U.S. Pat. No. 4,952,419 (applying a film of silicone oil to the surface of an implant and then contacting the silicone film bearing surface with antibiotic powders), and U.S. Pat. No. 5,624,704 (antibiotics are dissolved in solvent with alkanizing agents and penetrating agents and applied to a medical device surface), the disclosures of which are incorporated herein by reference.

According to a preferred antimicrobial treatment process, the desired antimicrobial agent or agents are first dissolved in an appropriate solvent or combination of solvents to form an antimicrobial solution. Suitable solvents in this regard include essentially any solvent that will effectively dissolve the antimicrobial agent or agents of interest, and that are conducive with the incorporation of the at least some of the dissolved antimicrobial agent into the medical device. The solvent is generally selected from one that will readily spread onto and/or along the particular annuloplasty ring surface to which it is applied. The degree of this spreading may be influenced by the surface tension of the solvent and by the surface characteristics and configuration of the material used to produce the medical device. Advantageously, the incorporation of the antimicrobial agents into the annuloplasty ring occurs in the substantial absence of additional constituents, e.g., penetrating agents, alkalinizing agents, etc., that have been conventionally used, e.g., in U.S. Pat. No. 5,624,704, for facilitating antimicrobial agent penetration and/or adherence into or onto the medical device. Illustrative examples of suitable solvents for use in this invention include, but are not necessarily limited to, $C_1$ to $C_6$ alcohols (e.g., methanol, ethanol, etc.), $C_1$ to $C_6$ ethers (e.g., tetrahydrofuran), $C_1$ to $C_6$ aldehydes, aprotic heterocyclics (e.g., n-methyl pyrrolidinone, dimethyl sulfoxide, dimethyl formamide), acetonitrile, acetic acid, and other like solvents.

The concentration of the antibiotic agent in the antibiotic solution is not specifically restricted. Optimal concentration ranges will likely vary depending upon the particular antimicrobial agent/solvent system used, on the conditions under which the antimicrobial solution is contacted with the annuloplasty ring, and on the particular component or components being treated, but can nonetheless be readily determined by the skilled individual in the art. In general, a higher concentration of an antimicrobial agent in the antimicrobial solution will result in greater incorporation into or onto the annuloplasty ring under an otherwise constant set of application conditions. However, an upper concentration limit will typically characterize a particular combination of antimicrobial solution and medical device, above which further antimicrobial incorporation will become limited. Generally, the concentration of the antimicrobial agent in the antimicrobial solution is essentially in the range of about 1 mg/ml to 60 mg/ml for each antimicrobial agent present in the composition.

The antimicrobial solution of the present invention is applied to, or otherwise contacted with, at least some portion of the annuloplasty ring of interest in order to effect incorporation of the antimicrobial agent into said portion. As will be apparent to the skilled individual in this art, the means by which the antimicrobial solution is contacted with the medical device is not critical, and may vary depending on the type and portion of device being treated, the area of the device being treated, etc. Typically, the biodegradable insert, the fabric sheath and/or the assembled annuloplasty ring will simply be dipped or otherwise immersed in an antimicrobial solution. Alternatively, the antimicrobial solution may be applied to the annuloplasty ring or the area of the annuloplasty ring being treated, e.g., by injection, flushing, spraying, etc. Other techniques for the contacting the antimicrobial solution with the annuloplasty ring will be readily apparent to the skilled individual in this art.

Subsequent to contacting the antimicrobial solution with the annuloplasty ring, the antimicrobial solution is generally allowed to remain in contact with the device for a duration and under conditions effective to cause a desired degree of incorporation of the antimicrobial agent into or onto the annuloplasty ring. The temperature of the solution during this treatment step is not critical, and can be essentially any temperature which does not adversely effect the desired antimicrobial agent incorporation. Excessively high temperatures should be avoided if they are in a range which can cause degradation of the antimicrobial agent. Furthermore, care should be taken when treating the device at temperatures that are sufficiently low since they may adversely impact the solubility of the antimicrobial agent(s) in the antimicrobial solution. A desired treatment temperature will typically be in the range of about 10 deg. C. to about 60 deg. C., more typically it will be in the range of about 20 deg. C. to about 50 deg. C. The duration of the treatment step is not specifically restricted, and may be in the range of 0.1 minutes to several hours or more. Typically, treatment duration in the range of about 0.1 hours to about 2 hours will result in a desirable degree of antimicrobial agent incorporation into the portion of the annuloplasty ring being treated. Of course, the optimal treatment time for a given application may vary depending on a number of parameters, e.g., the antimicrobial solution being used, reaction temperature, etc., but this can be readily determined by one skilled in the art.

The treated annuloplasty ring component or components are typically dried to eliminate any remaining solvent, e.g., by air-drying, heating, etc. After drying, the antimicrobial agent incorporated into or onto the desired portion of the annuloplasty ring is preferably not subject to substantial diffusion until implanted in vivo, or otherwise exposed to comparable environment, wherein the incorporated antimicrobial agent becomes redissolved, and therefore more subject to diffusion from the device into the surrounding environment.

The phrases "incorporation into" and "incorporating into," as used herein, means that the antimicrobial agent permeates, adheres to, or otherwise becomes associated with one or more polymeric structure of the annuloplasty ring. Thus, the antimicrobial agent may be largely associated with the surface of the ring insert and/or the fabric sheath, may penetrate within or between the polymeric structures that make up these components, etc. The nature of the association between the antimicrobial agent and the annuloplasty ring may depend on the antimicrobial agent, the solvent system, and/or the composition and structure of the annuloplasty ring being treated. The extent of incorporation of the antimicrobial agent into or onto the annuloplasty ring may be evaluated, for example, by simple mass analysis of the device before and after treatment. Alternatively, the incorporated antimicrobial agent can be extracted from the device using an appropriate solvent and analyzed by any one of a variety of suitable quantitative technique, e.g., high-performance liquid chromatography or ultraviolet/visible spectroscopy.

By practice of this preferred antimicrobial treatment process of the present invention, an annuloplasty ring is provided which exhibits the release of antimicrobial agent from at least some portion of the annuloplasty ring for a period of time after the annuloplasty ring has been implanted or otherwise exposed to an in vivo environment. The release profile of the antimicrobial agent from the annuloplasty ring may be evaluated using any one of a variety of approaches. For example, this may involve sequentially monitoring over time the diffusion of antimicrobial agent from the annuloplasty ring into a solution in which the device is immersed. The solution may be replaced at certain time points, and the quantity of antimicrobial agent evaluated at the various time points by a suitable analytic technique, such as high-performance liquid chromatography.

The annuloplasty ring treated in accordance with this invention preferably exhibits antimicrobial activity, i.e., the antimicrobial agent is released from the annuloplasty ring at sufficient levels to inhibit the growth of antimicrobial organisms adherent to the device or in close proximity thereto. The antimicrobial activity of the annuloplasty ring resulting from release of the antimicrobial agent may be evaluated by a variety of approaches. For example, zone of inhibition (ZOI) analyses, and other similar variations thereof, may be used (see, for example, Sherertz, et al. Antimicrobial Agents and Chemotherapy, August 1989, p.1174, 1989). Using this approach, a medical device is placed directly on an agar plate covered with growing bacteria. The plates are evaluated over time to determine the extent of bacterial growth in the agar surrounding the device. A bacterial free zone surrounding the device, called a zone of inhibition, is indicative of inhibition of bacterial growth by agents that have diffused from a treated medical device into the surrounding agar.

The antimicrobial release and/or activity from the annuloplasty ring is generally sustained for an extended number of days, or even weeks. In this way, the susceptibility to device infection may be inhibited for a clinically relevant duration following implantation in vivo. In an illustrative embodiment of the invention, the medical device of this invention will exhibit some degree of antimicrobial release and/or activity for at least a day, more typically for several days, and in some instances for up to a week or more, following exposure to an in vivo environment.

The following examples are provided to demonstrate certain illustrative embodiments of this invention. It should be appreciated by those skilled in the art that the techniques disclosed in the illustrative examples which follow represent those found by the inventors to function in the practice of the invention. However, those skilled in the art should, in light of the present disclosure, appreciate that many changes can be made in the specific embodiments which are disclosed and still obtain a like or similar result without departing from the spirit and scope of the invention.

EXAMPLE 1

PREPARATION OF ANTIMICROBIAL SOLUTIONS

A process was performed essentially in accordance with U.S. Pat. No. 5,624,704. Briefly, in a dark glass bottle, 40 ml of methanol was heated to about 45 deg. C. on a magnetic stirrer-hot plate and 0.2 g of sodium hydroxide was dissolved therein. Heating was removed and 5 g minocycline, 8 g rifampin, and 80 ml butyl acetate, were dispersed in the solvent. 20 ml aliquots of the mixture were transferred to glass beakers containing either a pre-weighed polyethylene terepthalate sewing cuff assembly (Carbomedics Prosthetic Heart Valve, CPHV™ 27 Mitral) or a polytetrafluoroethylene felt ring (27 Mitral), prepared at Sulzer Carbomedics Inc. (Austin, Texd.). The samples were incubated in the antimicrobial solutions for approximately 1.5 hours at about 45 deg. C. After incubation, the treated cuffs and felts were removed from the antimicrobial solution and air-dried overnight. After drying, each sample was weighed and transferred to a sterile bag. Exposure to light was minimized during and after the drying process until further studies were performed.

In an illustrative process according to the present invention, 2000 ml of methanol was added to a dark glass bottle and heated to about 45 deg. C. on a magnetic stirrer-hot plate. 5 g minocycline and 8 g rifampin were dispersed in the methanol. 20 ml aliquots of the mixture were transferred to glass beakers containing either a pre-weighed polyethylene terepthalate sewing cuffs (CPIIV™ 27 Mitral) or a polytetrafluoroethylene felt ring (27 Mitral), prepared at Sulzer Carbomedics Inc. The samples were incubated in the antimicrobial solutions for approximately 1.5 hours at about 45 deg. C. After incubation, the treated cuffs and felts were removed from their respective solutions and air-dried overnight. After drying, each sample was weighed and transferred to a sterile bag. Sample exposure to light was minimized during and after the drying process.

Table 1 below compares the formulations of the antimicrobial solutions used in producing minocycline/rifampin sewing cuffs and felts in accordance with either U.S. Pat. No. 5,624,704, or according to an illustrative example of the present invention. The antimicrobial solutions prepared according to U.S. Pat. No. 5,624,704 contained antimicrobial agents, an alkalinizing agent (e.g., sodium hydroxide), an organic solvent (e.g., methanol), and a penetrating agent (e.g., butyl acetate). In contrast, the illustrative antimicrobial solution of this invention contained only the antimicrobial agents dissolved in solvent (e.g., methanol).

TABLE 1

COMPARISON OF FORMULATIONS USED

| REAGENTS | U.S. Pat. No. 5,624,704 | PRESENT INENTION |
| --- | --- | --- |
| Sodium Hydroxide | 0.1% w/v | 0% |
| Methanol | 20% v/v | 100% v/v |
| Butyl Acetate | 80% v/v | 0% |
| Rifampin | 4% w/v | 4% w/v |
| Minocycline | 2.5% w/v | 2.5% w/v |

EXAMPLE 2

ANTIMICROBIAL AGENT INCORPORATION

Antibiotic incorporation into or onto the sewing cuff and felt samples was monitored by determining the change in mass before and after incorporation, and also by high-performance liquid chromatography (HPLC) analysis. For HPLC analysis, the dried samples were placed in glass beakers containing 30 ml of methanol, and this extraction solution was sonicated for about 30 minutes. The supernatant was poured into a dark glass jar. The extraction process was repeated up to three times and the extracts were combined and analyzed by HPLC using a Beckman Nouveau Gold HPLC system (Beckman Instruments; Fullerton, Calif.). The samples were diluted as necessary and injected in 0.1 M sodium phosphate, pH 3.2. 25 ul of each sample was injected by an auto sampler into the HPLC system. Sample separation was achieved using acetonitrile:water (4:6 v/v), with a flow rate of 1 ml/min, using a Water's C18 Nova Pak 60A, 4 um, 3.9×150 mm column, maintained at about 30 deg. C. Ultraviolet detection at 339 nm detected the minocycline and rifampin peaks at about 1.4 and 4.0 minutes, respectively, under these conditions. A calibration curve was generated using 1:1 mixtures of minocycline and rifampin in the mobile phase at a concentration range between 1 ug/ml and 100 ug/ml.

Table 2 below summarizes the results for total antibiotic incorporation into the sewing cuffs and felts treated according to U.S. Pat. No. 5,624,704, and according to the present invention. From these results, it is apparent that the method of the present invention achieves levels of antibiotic incorporation into the sewing cuffs and felts comparable to those observed for the method of U.S. Pat. No. 5,624,704. For the HPLC analysis, total incorporation values were calculated by adding the weight values obtained for minocycline and rifampin. The cuffs generally had higher loading compared with the felts, possibly due to the greater mass and surface area associated with the polyester material. The values obtained by the HPLC method were slightly lower compared with the values obtained by the total mass method. This may be attributed to the extraction method employed for HPLC sample preparation, which may not have been complete.

TABLE 2

ANTIBIOTIC INCORPORATION IN SEWING CUFFS AND FELTS

| SAMPLES | TOTAL LOADING BY WEIGHT (mg) | TOTAL LOADING BY HPLC (mg) |
| --- | --- | --- |
| Cuff (U.S. Pat. No. 5,624,704 | 112 | 105 |
| Cuff (methanol only) | 115 | 91 |
| Felt (U.S. Pat. No. 5,624,704) | 51 | 81 |
| Felt (methanol only) | 48 | 43 |

Ultraviolet spectra of minocycline and rifampin obtained during HPLC analysis demonstrated that they have distinctive $\lambda_{max}$ values of 350 and 334, respectively. The spectral properties observed did not change as a result of incorporation method (not shown), indicating that the compounds maintained their structure during the medical device treatment processes.

EXAMPLE 3

RELEASE PROFILES FOR RIFAMPIN AND MINOCYCLINE

The kinetics of antibiotic release from the treated samples was evaluated by incubating the samples in 15 ml phosphate buffered saline (PBS) at about 37 deg. C. for 30 days. For about the first hour, the samples were gently agitated in PBS at room temperature in 15 ml PBS. This PBS solution was removed and frozen until further analysis. Fresh PBS was added and the samples were placed in a 37 deg. C. incubator. The PBS was thereafter replaced at 1, 2, 4, 5, 7, 11, 15, 21, 25, and 30 days, and each aliquot was frozen until subsequent analysis by HPLC. The release profiles for rifampin and minocycline are summarized below in Tables 3 and 4, respectively.

TABLE 3

RELEASE OF RIFAMPIN (mg) OVER 30 DAYS

| Day collected | Cuff (U.S. 5,624,704) | Cuff (methanol only) | Felt (U.S. 5,624,704) | Felt (methanol only) |
| --- | --- | --- | --- | --- |
| 0 | 14.0 | 14.6 | 10.6 | 5.85 |
| 1 | 22.1 | 19.9 | 12.7 | 13.5 |
| 2 | 13.4 | 13.1 | 2.16 | 5.63 |
| 4 | 5.37 | 10.1 | 0.66 | 1.31 |
| 5 | 0.72 | 2.45 | 0.25 | 0.12 |

TABLE 3-continued

RELEASE OF RIFAMPIN (mg) OVER 30 DAYS

| Day collected | Cuff (U.S. 5,624,704) | Cuff (methanol only) | Felt (U.S. 5,624,704) | Felt (methanol only) |
|---|---|---|---|---|
| 7 | 0.29 | 0.59 | 0.16 | 0.02 |
| 11 | 0.25 | 0.20 | 0.08 | 0.01 |
| 15 | 0.20 | 0.06 | 0.04 | — |
| 21 | 0.17 | 0.02 | 0.02 | — |
| 25 | 0.13 | 0.02 | 0.01 | — |
| 30 | 0.07 | 0.01 | — | — |
| Avg.Total | 56.51 | 60.49 | 53.25 | 26.44 |

TABLE 4

RELEASE OF MINOCYCLINE (mg) OVER 30 DAYS

| Day collected | Cuff (U.S. 5,624,704) | Cuff (methanol only) | Felt (U.S. 5,624,704) | Felt (methanol only) |
|---|---|---|---|---|
| 0 | 11.6 | 15.8 | 8.25 | 4.8 |
| 1 | 7.43 | 8.70 | 3.53 | 0.75 |
| 2 | 2.18 | 1.13 | 0.33 | 0.1 |
| 4 | 0.92 | 1.01 | 0.11 | 0.02 |
| 5 | 0.15 | 0.09 | 0.05 | — |
| 7 | 0.05 | 0.06 | 0.05 | — |
| 11 | 0.05 | 0.03 | 0.02 | — |
| 15 | 0.04 | 0.02 | — | — |
| 21 | 0.08 | — | — | — |
| 25 | 0.02 | — | — | — |
| 30 | 0.01 | — | — | — |
| AvgTotal | 22.1 | 25.3 | 24.7 | 11.9 |

From the above examples, it is apparent that minocylcine and rifampin can be incorporated into medical devices according to the method of this invention without the need to include the penetrating agents and/or alkalinizing agents taught by U.S. Pat. No. 5,624,704 as necessary for effective antimicrobial agent incorporation. Moreover, the devices exhibited clinically desirable antimicrobial agent release characteristics.

EXAMPLE 4

INHIBITION OF DEVICE COLONIZATION AND INFECTION IN VIVO

Samples of polyethylene terepthalate fabric (DTH-2, Vascutek Inc., Renfrewshire, Scottland) were sewn around polytetrafluoroethylene felt (CR Bard Inc., Haverhill, Mass.) using silicone-treated, non-absorbable, braided polyester 4.0 sutures (Davis and Geck Inc., St.Louis, Mo.). Some of these sample assemblies were treated according to U.S. Pat. No. 5,624,704 by contacting them with a solution comprised of 40 mg/ml rifampicin, 25 mg/ml minocycline, and 1 mg/ml sodium hydroxide in 20% (v/v) methanol in butyl acetate. Other sample assemblies were treated with 40 mg/ml rifampicin and 25 mg/ml minocycline dissolved in methanol only. The samples were incubated in these solutions for approximately 1.5 hours at about 45 deg. C. After incubation, the samples were removed from their respective solutions and air-dried overnight.

The treated samples were inoculated with approximately $10^5$ CFU *Staphylococcus aureus* (P1 strain, a mutant of ATCC 25923), and implanted subcutaneously into rabbits. The samples were retrieved from the animals after one week after implantation. Device colonization was evaluated by culturing the retrieved device by rolling and/or dragging each side of the device on chocolate agar plates (BBL Media, Becton Dickinson Microbiology Systems, Cockeysvile, Me.). Device-related infection was evaluated by inoculating blood samples taken at the time of device retrieval on chocolate agar plates. Bacterial growth was assessed after incubating the plates for 48 hours at 37 deg. C. The results of these experiments are summarized in Table 5 below.

TABLE 5

|  | Untreated | U.S. Pat. No. 5,624,704 | Methanol only |
|---|---|---|---|
| Device Colonization | 25/31 | 2/30 | 1/34 |
| Device-related Infection | 25/31 | 0/30 | 0/34 |

These results demonstrate the in vivo efficacy of medical devices treated in accordance with this invention. In particular, protection from device colonization and device-related infection was comparable, if not improved, relative to a group of samples treated according to U.S. Pat. No. 5,624,704. The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. An annuloplasty ring comprising:
   a ring insert at least partly comprised of a surface eroding biodegradable polymer material;
   an elastomeric sheath enclosing said ring insert; and
   a fabric sheath enclosing said ring insert and said elastomeric sheath.

2. The annuloplasty ring of claim 1, wherein the surface eroding biodegradable polymer material comprises a polyanhydride.

3. The annuloplasty ring of claim 1, wherein the surface eroding biodegradable polymer material comprises a photopolymerizable polyanhydride.

4. The annuloplasty ring of claim 1, wherein the surface eroding biodegradable polymer material comprises a polyanhydride polymerized from methacrylate anhydride monomers.

5. The annuloplasty ring of claim 4, wherein the methacrylate anhydride monomers are synthesized from diacid molecules of sebacic acid or 1,6-bis(p-carboxyphenoxy)-hexane.

6. The annuloplasty ring of claim 4, wherein the surface eroding biodegradable polymer material comprises a copolymer of methacrylate anhydride monomers synthesized from diacid molecules of sebacic acid and 1,6-bis(p-carboxyphenoxy)-hexane.

7. The annuloplasty ring of claim 1, wherein the elastomeric sheath is comprised of a silicone rubber, a poly(ether urethane) or a polytetrafluoroethylene.

8. The annuloplasty ring of claim 1, wherein the ring insert further comprises one or more plasticizers, stabilizers, pigments, dyes, radio-opaque materials, lubricants, antioxidants, bioactive agents or antithrombogenic agents.

9. The annuloplasty ring of claim 1, wherein said annuloplasty ring further comprises at least one antimicrobial agent incorporated into the fabric sheath of the annuloplasty ring by dissolving the antimicrobial agent in a solvent to form an antimicrobial solution consisting of said antimicrobial agent and said solvent and contacting the antimicrobial solution with at least some portion of the fabric sheath of the annuloplasty ring.

10. The annuloplasty ring of claim 9, wherein said solvent is selected from the group consisting of alcohols, ethers, aldehydes, acetonitrile, acetic acid, and aprotic heterocyclics.

11. The method of claim 9, wherein said solvent is selected from the group consisting of methanol, ethanol, or n-methyl pyrrolidinone.

12. The annuloplasty ring of claim 9, wherein the fabric sheath is comprised of a polymeric material.

13. The annuloplasty ring of claim 9, wherein the fabric sheath is comprised of a polymeric material selected from the group consisting of polyethyleneterephthalate, polytetrafluoroethylene and polyester (polyacetate).

14. A method for making an annuloplasty ring comprising:
    forming a ring insert at least partly comprised of a surface eroding biodegradable polymer material;
    enclosing at least a portion of said ring insert in an elastomeric sheath and
    enclosing at least a portion of said ring insert and said elastometeric sheath within a fabric sheah.

15. The method of claim 14, wherein the surface eroding biodegradable polymer material comprises a oilyanhydride.

16. The method of claim 14, further comprising
    dissolving at least one antimicrobial agent in a solvent to form an antimicrobial solution;
    contacting the antimicrobial solution with at least some portion of the fabric sheath of the annuloplasty ring; and
    evaporating said solvent to deposit said at least one antimicrobial agent in said fabric sheath.

17. The method of claim 16, wherein the solvent is selected from the group consisting of alcohols, ethers, aldehydes, acetonitrile, acetic acid, and aprotic heterocyclics.

18. The method of claim 16, wherein the solvent is selected from the group consisting of methanol, ethanol, or n-methyl pyrrolidinone.

19. The method of claim 14, wherein the ring insert is formed by molding, extrusion or machining the surface eroding biodegradable polymer material.

20. The method of claim 14, wherein the surface eroding biodegradable polymer material comprises a photopolymerizable polyanhydride.

21. The method of claim 14, wherein the surface eroding biodegradable polymer material comprises a polyanhydride polymerized from methacrylate anhydride monomers.

22. The method of claim 21, wherein the methacrylate anhydride monomers are synthesized from diacid molecules of sebacic acid or 1,6-bis(p-carboxyphenoxy)-hexane.

23. The method of claim 21, wherein the biodegradable material comprises a copolymer of methacrylate anhydride monomers synthesized from diacid molecules of sebacic acid and 1,6-bis(p-carboxyphenoxy)-hexane.

24. The method of claim 16, wherein the fabric sheath is comprised of a polymeric material.

25. The method of claim 16, wherein the fabric sheath is comprised of a polymeric material selected from the group consisting of polyethyleneterephthalate, polytetrafluoroethylene and polyester (polyacetate).

26. The method of claim 14, wherein the elastomeric sheath is comprised of a silicone rubber, a poly(ether urethane) or a polytetrafluoroethylene.

27. The method of claim 14, wherein the ring insert further comprises one or more plasticizers, stabilizers, pigments, dyes, radio-opaque materials, lubricants, antioxidants, bioactive agents or antithrombogenic agents.

28. An annuloplasty ring produced according to the method of claim 14.

* * * * *